(12) United States Patent
Antonicek et al.

(10) Patent No.: US 6,291,515 B1
(45) Date of Patent: Sep. 18, 2001

(54) USE OF EFOMYCINS

(75) Inventors: Horst-Peter Antonicek, Bergisch Gladbach; Erwin Bischoff, Wuppertal; Daniel Gondol, Bergisch Gladbach; Oliver Gutbrod, Odenthal; Thomas Krahn, Hagen; Maria-Luisa Rodriguez, Erkrath; Helmuth Schütz, Regensburg, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/267,322

(22) Filed: Mar. 12, 1999

(30) Foreign Application Priority Data

Dec. 23, 1996 (DE) ............................................. 196 54 073

(51) Int. Cl.[7] ....................... A61K 31/365; C07D 321/00
(52) U.S. Cl. ............................................. 514/450; 549/267
(58) Field of Search .............................. 549/267; 514/450

(56) References Cited

U.S. PATENT DOCUMENTS

| | | | |
|---|---|---|---|
| 4,927,810 | 5/1990 | Frobel et al. | 514/23 |
| 5,185,326 | 2/1993 | Muller et al. | 514/23 |
| 5,233,029 | 8/1993 | Hammann et al. | 536/7.1 |

FOREIGN PATENT DOCUMENTS

| | | |
|---|---|---|
| 38 31 695 A1 | 3/1990 | (DE) . |
| 0 197 360 B1 | 10/1986 | (EP) . |
| 0 236 894 B1 | 9/1987 | (EP) . |
| 0 461 499 A2 | 12/1991 | (EP) . |

OTHER PUBLICATIONS

Journal of Antibiotics vol. XLIII, No. 11, S. 1431–1440, Nov./1990.

*Primary Examiner*—Ba K. Trinh
(74) *Attorney, Agent, or Firm*—Norris McLaughlin & Marcus

(57) ABSTRACT

The present invention relates to the use of known efomycins and elaiophylins for the treatment of autoimmune disorders, to new natural substances efomycins M and T, and processes for their preparation; in particular to their use as medicaments in psoriasis therapy.

9 Claims, No Drawings

USE OF EFOMYCINS

The present invention relates to the use of known efomycins and elaiophylins for the treatment of autoimmune disorders, to new natural substances efomycins M and T, and processes for their preparation; in particular to their use as medicaments in psoriasis therapy.

It is already known that efomycins and elaiophylins, in addition to their growth-promoting properties, also have an antiviral, antibacterial and anti-inflammatory action [cf. for this EP 461 499; DE 38 31 659 A1; The Journal of Antibiotics Vol. XLIII, No. 11, pp. 1431–1440].

Surprisingly, it has now been found that efomycins of the general formula (I)

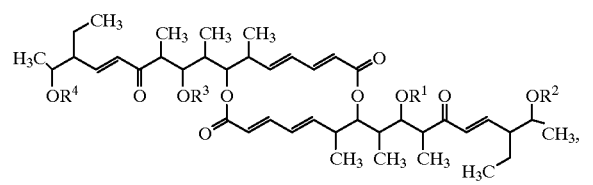

in which $R^1$, $R^2$, $R^3$ and $R^4$ are identical and represent hydrogen or the radical of the formula —CO—CH$_3$, surprisingly have a strongly inhibiting action on the adhesion of leukocytes, immunomodulatory effects with involvement of lymphocytes and showed no cytotoxicity whatsoever and are thus suitable for the treatment of autoimmune disorders, in particular for the treatment of psoriasis.

The compounds of the general formula (I) can exist in stereoisomeric forms, which either behave as image and mirror image (enantiomers), or which do not behave as image and mirror image (diastereomers). The invention relates both to the enantiomers and diastereomers or to their respective mixtures. Like the diastereomers, the racemic forms can also be separated using known methods into the stereoisomerically uniform constituents.

The present invention moreover relates to the new substances of the general formulae (Ia) and (Ib) having the configuration indicated here (Ia)

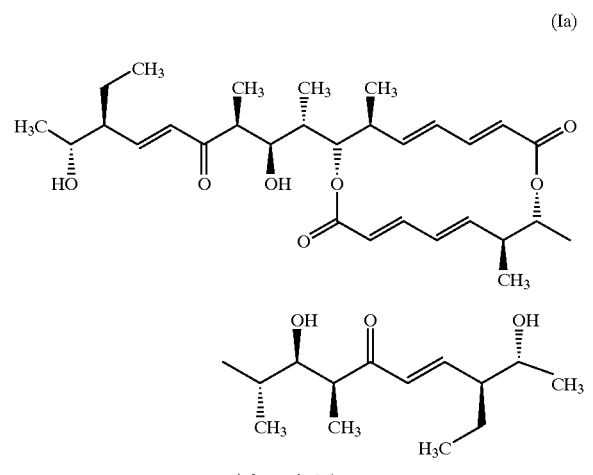

(efomycin M)

(Ib)

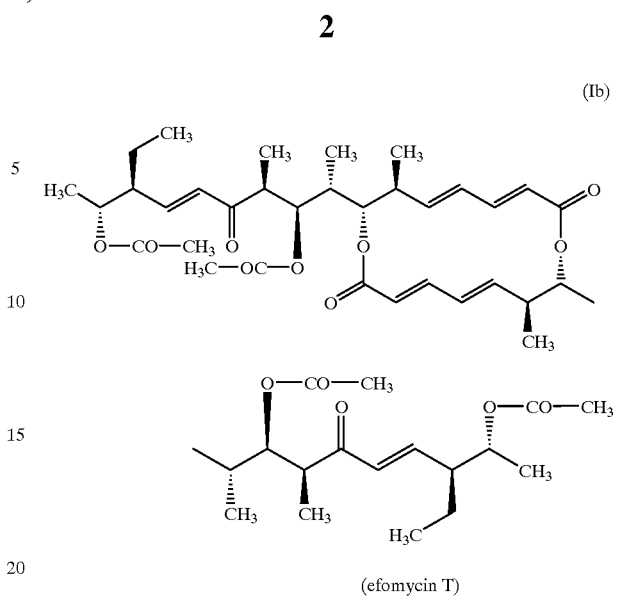

(efomycin T)

The known compounds of the general formula (I) according to the invention can be prepared by published methods.

The new compounds efomycins M (Ia) and T (Ib) can be prepared by first subjecting the mixture isolated from a complex macrodiolide, comprising efomycins A and G, of the general formula (II)

(II)

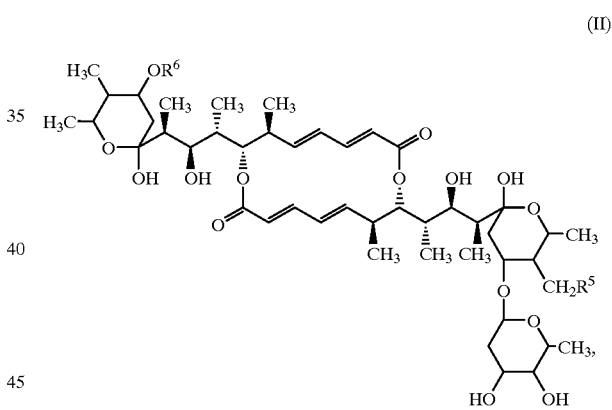

in which $R^5$ represents methyl and $R^6$ represents a radical of the formula

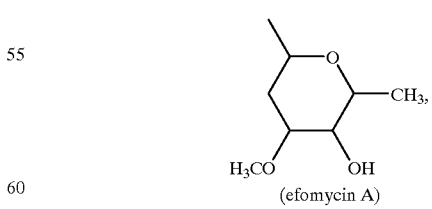

(efomycin A)

or $R^5$ represents methyl and $R^6$ represents a radical of the formula

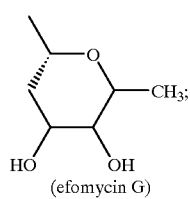

(efomycin G)

to a base-catalysed deglycosylation with β-elimination of the deoxyfucose side chains (efomycin M) and, in the case of the compound of the formula (IIb/efomycin T), carrying out an acetylation under mild conditions.

The process according to the invention can be illustrated by way of example by the following reaction scheme:

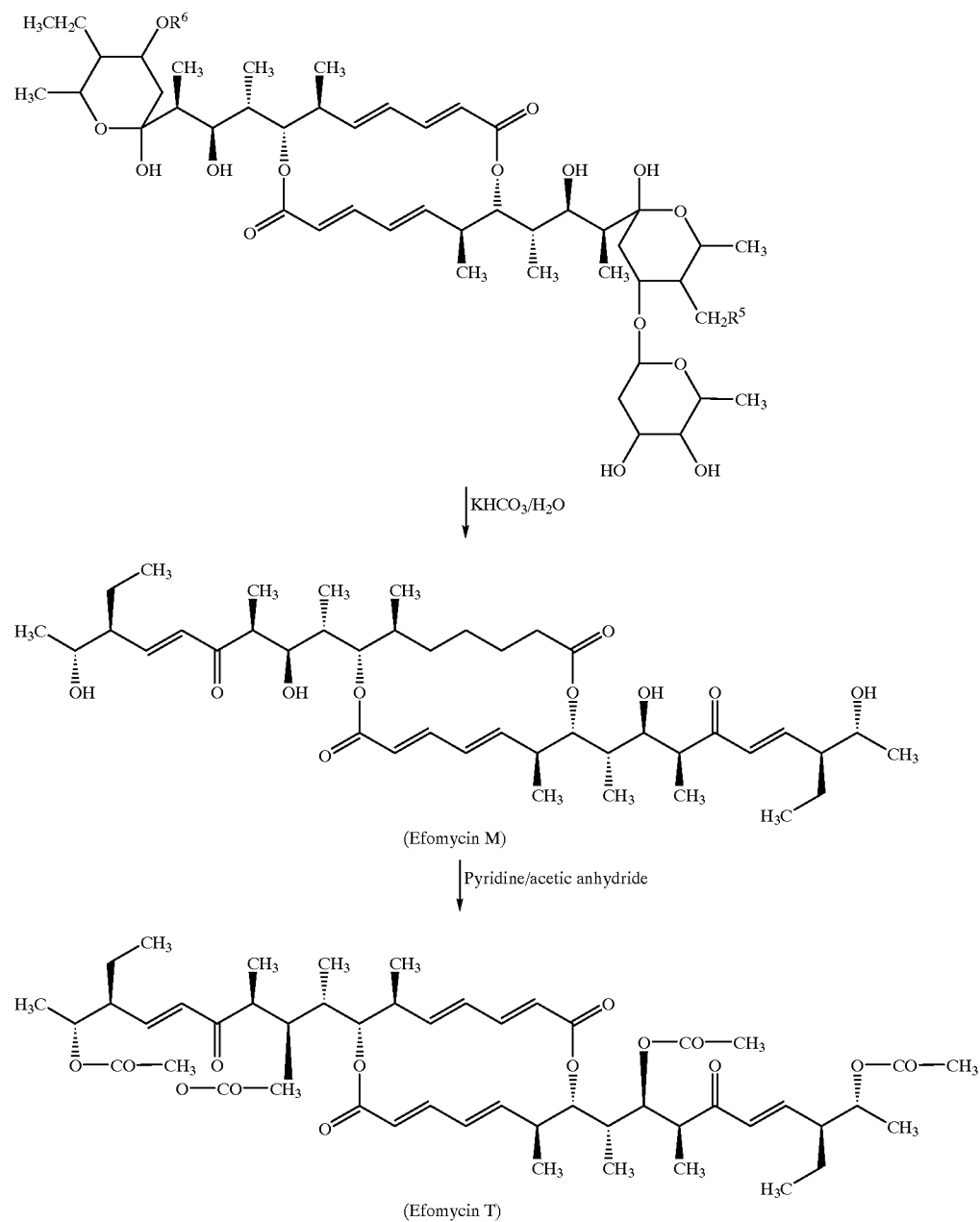

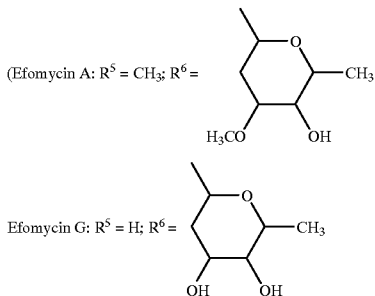

(Efomycin A: $R^5 = CH_3$; $R^6 =$ [sugar shown])

Efomycin G: $R^5 = H$; $R^6 =$ [sugar shown]

Suitable solvents for the preparation of efomycin M are water and alcohols such as methanol, ethanol, propanol, and/or ethyl acetate and mixtures thereof. The system water/ethanol/ethyl acetate is preferred.

Suitable bases for this step in general are the customary inorganic or organic bases. These preferably include alkali metal hydroxides such as, sodium or potassium hydroxide, or alkali metal carbonates such as sodium or potassium carbonate, or alkali metal hydrogencarbonates such as sodium or potassium hydrogencarbonate, or alkali metal alkoxides such as, sodium or potassium ethoxide.

The base is used in an amount from 1 mol to 5 mol, preferably from 1 mol to 2 mol, relative to 1 mol of the compounds of the general formula (II). Potassium hydrogencarbonate is preferred.

The reaction can be carried out at normal, elevated or reduced pressure (e.g. 0.5 to 5 bar). In general, it is carried out at normal pressure.

The reaction is carried out at the reflux temperature of the corresponding alcohol.

The acetylation is carried out under protective gas atmosphere in pyridine using acetic anhydride, if appropriate in the presence of 4-(N,N-dimethylamino)pyridine, at room temperature.

The compounds of the general formula (II), efomycins A and G, are known [cf. EP 197 360; EP 236 894 and EP 461 499].

The compounds of the general formula (I) and the new substances of the formulae (Ia)/(Ib) (efomycins M and T) show an unforeseeable spectrum of pharmacological action.

Their action consists in the reduction or complete inhibition of the adhesion of leukocytes and the immunomodulatory effects with involvement of lymphocytes, in particular the T lymphocytes. Moreover, they have excellent pharmacokinetics and, due to the absence of the sugar residue typical of these structures, they show no cytotoxicity whatsoever on endothelial cells in the MTT test [MTT=(3-[4,5-di-methylthiazol- 2-yl]-2,5-diphenyltetrazolium bromide; or Thiazolyl Blue] at efficacious concentrations. The MTT test is well-known in the art. It was carried out with a test kit which is commercially available (e.g. "Cell growth determination kit MTT based", Stock No. CGD-1 from Sigma Chemical).

They are therefore suitable for the prophylaxis and treatment of autoimmune disorders. These include psoriasis, acute and chronic disorders such as, thyroiditis, inflammatory bowel disorders, inflammations of the gastrointestinal tract, primary liver cirrhosis, or psoriasis, multiple sclerosis, myasthenia, lupus erythematosus, Basedow's disease, Hashimoto's disease, transplant rejection and autoimmune haemolytic anaemia. The prophylaxis and treatment of psoriasis is preferred.

Inhibition of PMNL Adhesion to Hypoxia-Stimulated Pig Aortas

Freshly isolated pig aortas were brought into the laboratory from the local slaughterhouse in oxygen-aerated, phosphate-buffered saline solution (PBS). Freshly obtained pig or human blood was taken for the preparation of polymorphonuclear neutrophilic granulocytes (PMNL). The aortas were stimulated by placing them for 30 minutes in PBS which was aerated with nitrogen (hypoxia stimulus). The aorta were then fixed between a Teflon block (below) and a specially made steel plate (above) with drilled wells (similar to a microtiter plate). PMNL and the potential adhesion inhibitors were added to the luminal side, i.e. to the stimulated endothelial cell layer, in cell media (M199, Gibco). After a 90-minute coincubation at 37° C. in an incubator, the wells were washed. The remaining adherent PMNL were lysed. The activity of the PMNL-specific myeloperoxidase (MPO) in the lysate was determined photometrically and compared to the untreated control (only solvent). Table [A] shows the inhibition of the action of the efomycins. The proportion of the adherent PMNL in comparison with the control is indicated.

Table [A]:

Inhibition of the adhesion of pig PMNL or human PMNL to hypoxia-stimulated pig aorta by efomycins

|  | % adherent PMNL | |
| --- | --- | --- |
|  | Pig PMNL | Human PMNL |
| Control | 100 | 100 |
| Ex. No. 1 (efomycin M) | 33 ± 23 | 52 ± 2 |
| Ex. No. 2 (efomycin T) | 85 ± 11 | 90 ± 5 |

Surprisingly, efomycin M (Ia), which does not inhibit the adhesion of PMNL to albumin-coated plastic surfaces, was active in the test model described. The adhesion test to albumin-coated plastic surfaces is described in detail, inter alia, in EP 0 461 499 A2 (Use Example 1). In an MTT test, efomycin M (Ia) showed no cytotoxicity against cultured endothelial cells.

The present invention also includes pharmaceutical preparations which, in addition to inert, non-toxic, pharmaceutically suitable auxiliaries and excipients, contain one or more compounds of the general formulae (I)/(Ia)/(Ib), or which consist of one or more active compounds of the formulae (I)/(Ia)/(Ib), and processes for the production of these preparations.

The active compounds of the formulae (I)/(Ia)/(Ib) should be present in these preparations in a concentration of 0.1 to 99.5% by weight, preferably 0.5 to 95% by weight, of the total mixture.

In addition to the active compounds of the formulae (I)/(Ia)/(Ib), the pharmaceutical preparations can also contain other pharmaceutical active compounds.

The above-mentioned pharmaceutical preparations can be prepared in a customary manner using known methods, for example using the auxiliary(ies) or excipient(s).

In general, it has proved advantageous to administer the active compound(s) of the formula(e) (I)/(Ia)/(Ib) in total amounts of approximately 0.01 to approximately 100 mg/kg, preferably in total amounts of approximately 1 mg/kg to 50 mg/kg, of body weight every 24 hours, if appropriate in the form of individual doses, to achieve the desired result.

However, if appropriate, it may be advantageous to depart from the amounts mentioned, namely depending on the species and body weight of the subject treated, on the individual behaviour towards the medicament, the nature and severity of the disorder, the type of preparation and administration, and the time or interval at which administration takes place.

$^1$H-NMR and $^{13}$C data are available for the two compounds Examples 1 and 2.

EXAMPLE 1

Efomycin M

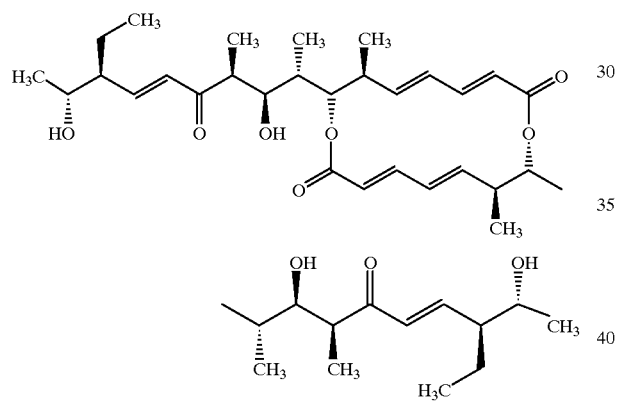

1 g of the mixture of efomycins A and G is refluxed for 6 hours with 2.5 g of potassium hydrogencarbonate in 15 ml of water, 5 ml of ethanol and 7 ml of ethyl acetate. The organic phases are combined, washed once with water and evaporated. The residue which remains is chromatographed on silica gel using chloroform:methanol 8:1. The fractions are analysed by thin-layer chromatography. The title compound is isolated from a mixture consisting of two further components and characterized by FAB-MS and $^1$H-NMR data.

| $^3$J coupling constants | |
|---|---|
| | Efomycin M |
| H3-H4 | 11.0 |
| H4-H5 | 14.5 |
| H5-H6 | 9.7 |
| H6-H7 | 10.5 |
| H7-H8 | 1.2 |
| H8-H9 | 6.5 |
| H9-H10 | 3.5 |

| $^3$J coupling constants | |
|---|---|
| | Efomycin M |
| H12-H13 | 16.0 |
| H13-H14 | 9.5 |
| H14-H15 | 7.0 |

EXAMPLE 2

Efomycin T

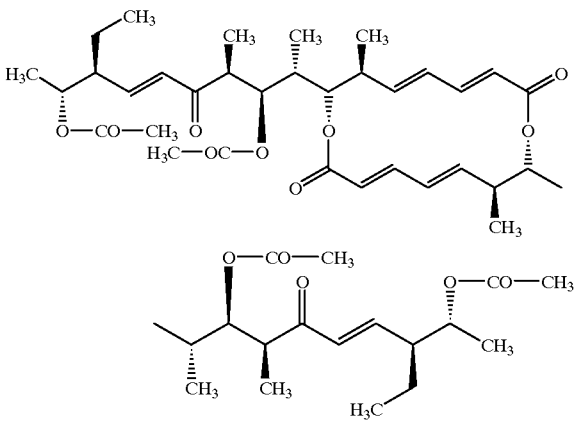

The title compound is prepared by reaction of 2 mg of the compound from Example 1 in 300 μl of pyridine and acetic anhydride (1:1) and allowed to stand overnight at room temperature. The solvent is then removed in vacuo, and the residue which remains is analysed by $^1$H-NMR and FAB-MS data.

| $^3$J coupling constants | |
|---|---|
| | Efomycin T |
| H3-H4 | 11.1 |
| H4-H5 | 15.1 |
| H5-H6 | 9.6 |
| H6-H7 | 10.3 |
| H7-H8 | 1.9 |
| H8-H9 | 9.1 |
| H9-H10 | 3.8 |
| H12-H13 | 15.2 |
| H13-H14 | 11.0 |
| H14-H15 | 4.8 |

What is claimed is:

1. A method of treating an autoimmune disorder in a patient comprising administering to said patient an effective amount therefor of an efomycin of the formula:

9

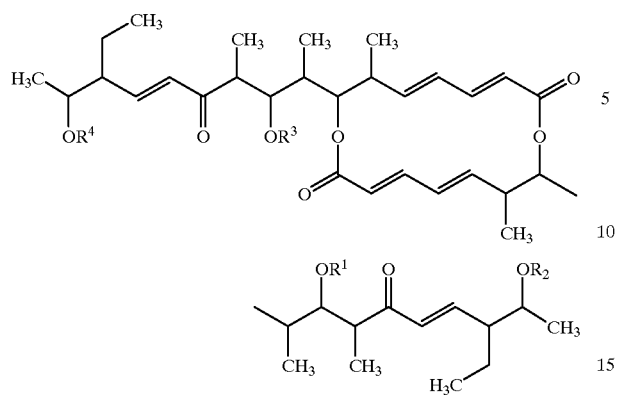

in which

R$^1$, R$^2$, R$^3$ and R$^4$ are identical and represent hydrogen or the radical of the formula —CO—CH$_3$, or of a purified stereoisomer or stereoisomer mixture thereof.

2. A compound selected from the group consisting of:
a) Efomycin M of the formula (Ia):

(Ia)

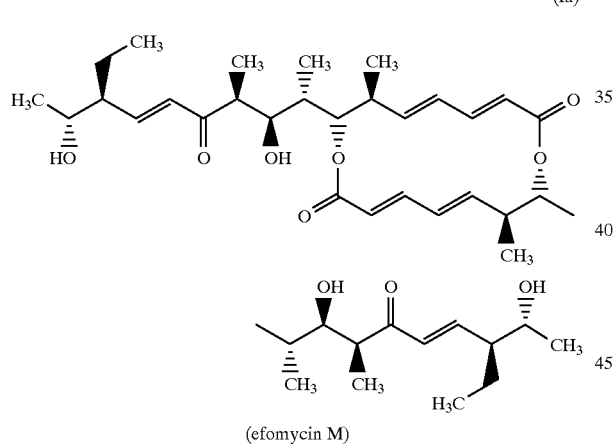

(efomycin M)

and b) Efomycin T of the formula (Ib):

(Ib)

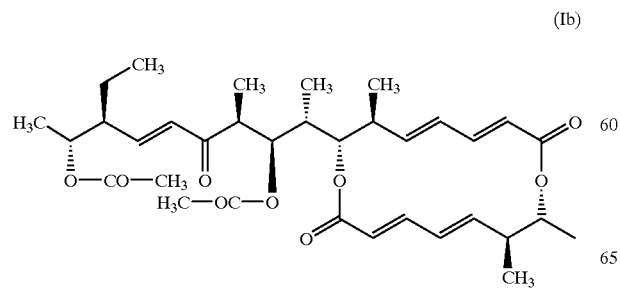

10

-continued

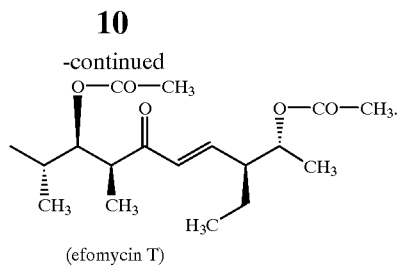

(efomycin T)

3. A composition for treating an autoimmune disorder comprising an effective amount therefor of a compound according to claim 2 and a pharmaceutically acceptable carrier.

4. A method according to claim 1, wherein the autoimmune disorder is psoriasis.

5. Method of treating an autoimmune disorder in a patient comprising administering to said patient an effective amount therefor of a compound according to claim 2.

6. A method according to claim 5, wherein the autoimmune disorder is psoriasis.

7. Compound of claim 2, being Efomycin M of the formula (Ia)

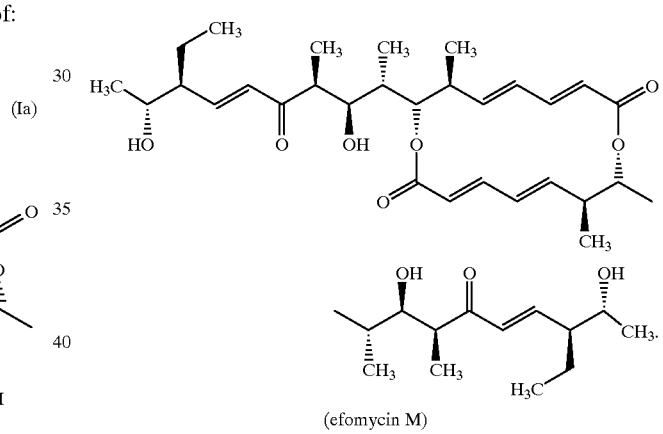

(efomycin M)

8. Compound of claim 2, being Efomycin T of the formula (Ib)

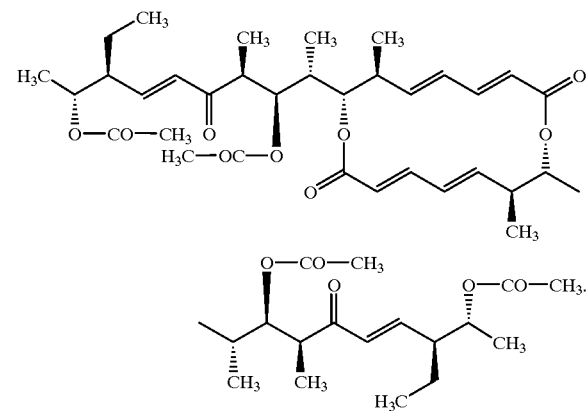

(efomycin T)

9. Process for the preparation of efomycin M (Ia) and/or of efomycin T (Ib) according to claim 2, characterized in that a mixture, comprising efomycins A and G of the general formula (II)

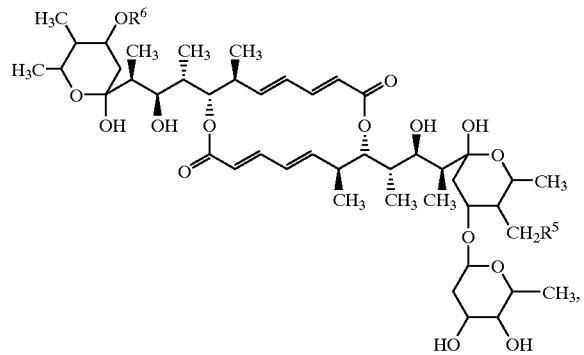

(II)

in which

R⁵ represents methyl and

R⁶ represents a radical of the formula

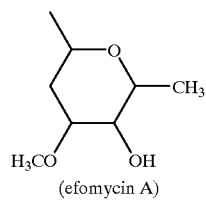

(efomycin A)

or

R⁵ represents methyl and

R⁶ represents a radical of the formula

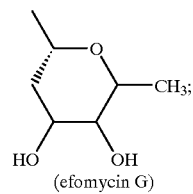

(efomycin G)

is first subjected to a base-catalysed deglycosylation with β-elimination of the deoxyfucose side chains and the efomycin M thus obtained is optionally acetylated under mild conditions for the preparation of efomycin T.

* * * * *